US00PP24625P2

(12) United States Plant Patent
Dean

(10) Patent No.: US PP24,625 P2
(45) Date of Patent: Jul. 8, 2014

(54) ***HOSTA* PLANT NAMED 'ECLIPSE'**

(50) Latin Name: *Hosta hybrida*
Varietal Denomination: ECLIPSE

(76) Inventor: Donald Dean, Ramsey, MN (US)

( * ) Notice: Subject to any disclaimer, the term of this patent is extended or adjusted under 35 U.S.C. 154(b) by 193 days.

(21) Appl. No.: 13/507,615

(22) Filed: Jul. 12, 2012

Related U.S. Application Data

(60) Provisional application No. 61/572,778, filed on Jul. 22, 2011.

(51) Int. Cl.
*A01H 5/00* (2006.01)

(52) U.S. Cl.
USPC ..... Plt./353

(58) Field of Classification Search
CPC ..... A01H 5/12; A01H 5/02
USPC ..... Plt./353
See application file for complete search history.

*Primary Examiner* — June Hwu

(57) ABSTRACT

A new cultivar of *Hosta* named 'ECLIPSE' that is characterized by upright, clumping habit, early summer white flowers, giant medium blue-green leaves with golden-yellow edges that brighten as the season progresses. In combination these traits set 'ECLIPSE' apart from all other existing varieties of *Hosta* known to the inventor.

2 Drawing Sheets

Genus: *Hosta.*
Species: *hybrida.*
Denomination: 'ECLIPSE'.

BACKGROUND OF THE INVENTION

This application claims the benefit of priority under 35 U.S.C. 119(e) of U.S. Provisional application No. 61/572,778 filed on Jul. 22, 2011, entitled *Hosta* Plant Named 'ECLIPSE'.

The present invention relates to a new and distinct cultivar of *Hosta* known commonly as plantain lily and grown for use in garden and landscape. The new cultivar is of the family Liliaceae, known botanically as *Hosta hybrida* and will hereinafter be referred to by the cultivar name 'ECLIPSE'.

'ECLIPSE' was discovered by the inventor in Ramsey, Minn., United States as a lateral bud sport of the parent an individual *Hosta* 'Solar Flare' (U.S. Plant Pat. No. 7,046). The parent is growing in loam soil in the inventor's landscape. The inventor selected 'ECLIPSE' in 2000 based on the criteria of unique foliage color atypical to the giant class of *Hosta*. The closest comparison variety is 'Solar Flare'. 'ECLIPSE' is distinguishable from the parent by foliage color, resistance to scorching, and undulate leaf edges.

'ECLIPSE' is an herbaceous perennial, exhibiting upright clumping habit, giant leaves of medium blue-green color with irregular golden-yellow edges that brighten as the season progresses. The edge of the leaf is conspicuously undulate, while the surface of a mature leaf is corrugated. Racemes of near white flowers bloom early summer to midsummer. Plant dimensions are 1.2 meter in width and 71 cm in height. Cultivation requirements are partial to full shade, moist well-draining soils, and moderate water. 'ECLIPSE' is resistant to snails and slugs due to the heavy substance of the foliage. Plant hardiness is classified as USDA Zone 3.

First asexual propagation of 'ECLIPSE' was conducted by the inventor in 2000 at the inventor's nursery in Ramsey, Minn., United States. Asexual propagation was accomplished using the method of division. Since that time under careful observation, the distinguishing characteristics of 'ECLIPSE' have been determined fixed, stable, uniform, and have been shown to reproduce true to type in successive generations of asexual propagation.

SUMMARY OF THE INVENTION

The following traits have been repeatedly observed and represent the distinguishing characteristics of 'ECLIPSE'. These traits in combination distinguish 'ECLIPSE' from all other existing varieties of *Hosta* known to the inventor. 'ECLIPSE' has not been tested under all possible conditions and phenotypic differences may be observed with variations in environmental, climatic, and cultural conditions, however, without any variance in genotype.

1. 'ECLIPSE' exhibits upright, clumping habit.
2. The leaves of 'ECLIPSE' are medium blue-green in color, with golden-yellow edges that brighten as the season progresses.
3. Foliage of 'ECLIPSE' exhibits conspicuously undulate edges, corrugated surfaces, and heavy substance, resulting in more resistance to slug activity than is typical of the species.
4. 'ECLIPSE' exhibits giant leaves typically 41 cm in length and 29.50 cm in width.
5. 'ECLIPSE' is strongly resistant to scorching.
6. 'ECLIPSE' bears racemes of near white flowers early summer to mid summer.
7. 'ECLIPSE' reaches 71 cm in height and 1.2 meter in width at maturity.
8. 'ECLIPSE' tolerates a wide range of soils, preferring moist well-draining soil in light to full shade.
9. 'ECLIPSE' is hardy to USDA Zone 3.

BRIEF DESCRIPTION OF THE DRAWINGS

The accompanying color drawings illustrate the overall appearance of the new *Hosta* variety named 'ECLIPSE' showing color of foliage and flower as true as it is reasonably possible to obtain in color reproductions of this type.

Drawing labeled

Drawing labeled

Figure 1:
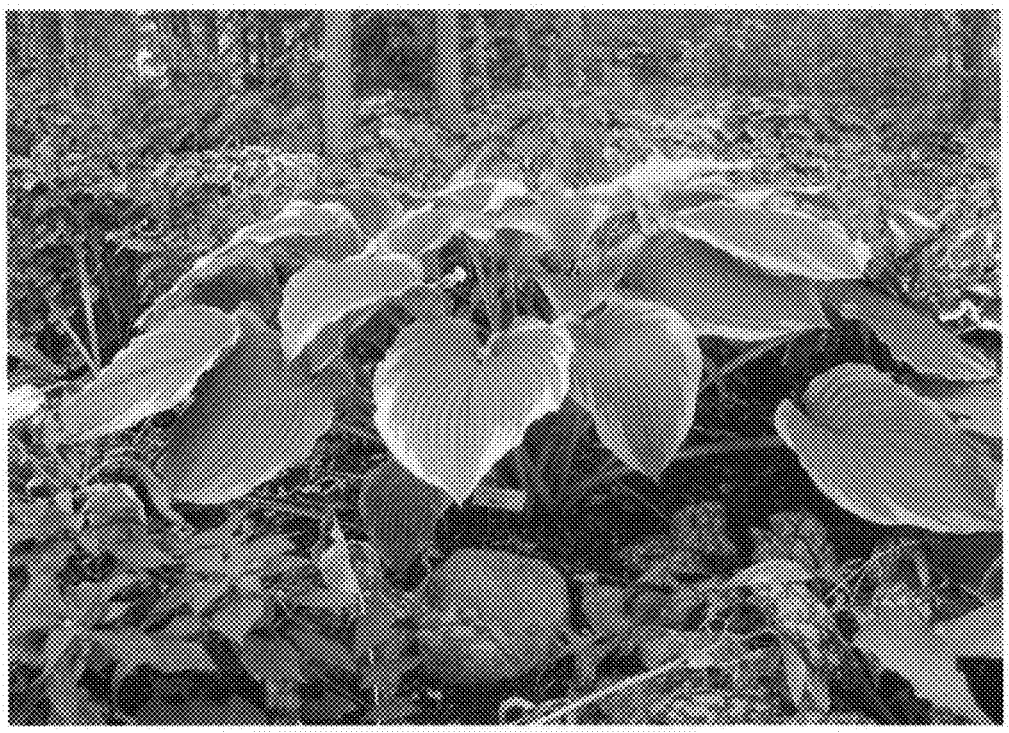
FIG. 1 depicts a 6-year-old plant growing out-of-doors in the inventor's garden in Ramsey, Minn.
Figure 2:
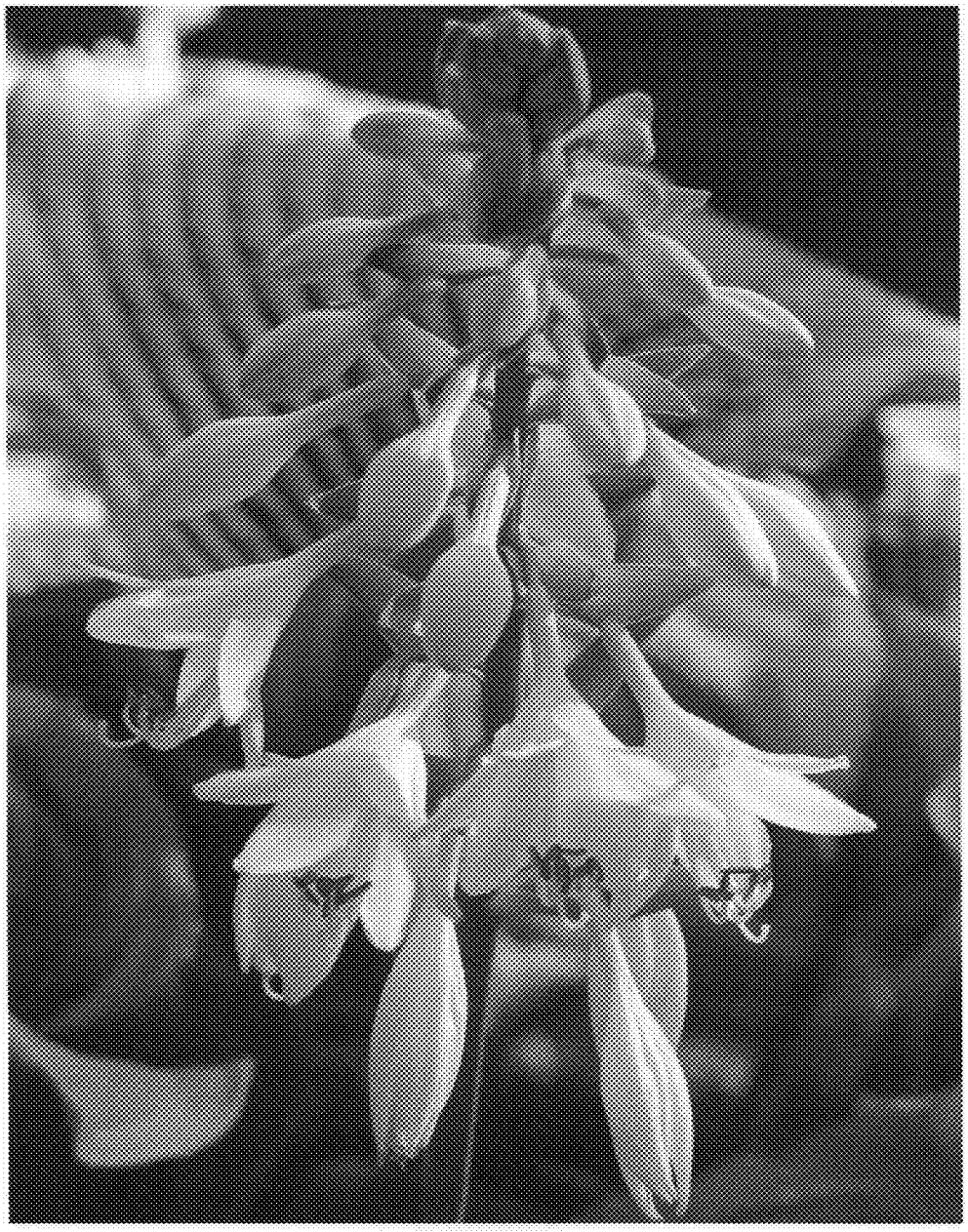
FIG. 2 depicts the flower of 'ECLIPSE'.

Color in the drawings may differ from the color values cited in the detailed botanical description, which accurately describe the actual colors of 'ECLIPSE'. Drawings were made using conventional photographic techniques and although flower and foliage color may appear different from actual color due to light reflectance, they are as accurate as possible by conventional photography.

BOTANICAL DESCRIPTION OF THE PLANT

The following is a detailed description of the new *Hosta* cultivar named 'ECLIPSE'. Color determinations are in accordance with The 2001 Royal Horticultural Society Colour Chart except where general color terms of ordinary dictionary significance are used. The growing requirements are similar to the species.

Family: Liliaceae.
Botanical classification: *Hosta hybrida* 'ECLIPSE'.
Genus: *Hosta.*
Species: *Hybrida.*
Denomination: 'ECLIPSE'.
Common name: Plantain lily.
Commercial classification: Herbaceous perennial.
Vigor: Medium vigor.
Use: Suitable for woodland garden, landscape, and as a container plant.
Parentage: *Hosta hybrida* 'ECLIPSE' was discovered as a sport of the parent an individual *Hosta* 'Solar Flare' (U.S. Plant Pat. No. 7,046).
Growth habit: Upright, clumping habit.
Plant height (at maturity): 71 cm in height.
Plant width (at maturity): 1.2 meter in width.
Hardiness: USDA Zone 3.
Asexual propagation: Division.
Root system: Fleshy.
Cultural requirements: Part shade or full shade in moist well-draining soil, with moderate water.
Cropping time: Approximately 12 months from division to a 1-litre container.
Seasonal interest: Medium blue-green foliage with golden-yellow margins that brighten as season progresses, and white flowers in early summer.
Diseases and pests: Resistant to scorching and slugs.
Special growing considerations: Avoid overhead irrigation. Avoid allowing plant to dry out particularly in containers.
Foliage:
- *Type.*—Winter dormant.
- *Leaf quantity* (*range*).—22-25 in number.
- *Leaf shape.*—Broadly ovate.
- *Leaf form.*—Arching.
- *Leaf substance.*—Heavy.
- *Branching habit.*—Basal.
- *Leaf apex.*—Acute.
- *Leaf base.*—Cordate.
- *Leaf division.*—Simple.
- *Leaf margin.*—Conspicuously undulate.
- *Golden-yellow margin dimensions* (*range*).—2.50 cm to 6 cm in width.
- *Leaf color* (*abaxial surface*).—138B and 162A fading to 162D.
- *Leaf color* (*adaxial surface*).—138A and 162A fading to 162D.
- *Leaf surface* (*abaxial surface*).—Corrugated.
- *Leaf surface* (*adaxial surface*).—Corrugated.
- *Venation pattern.*—Parallel.
- *Vein appearance* (*abaxial surface*).—Protruding.
- *Vein appearance* (*adaxial surface*).—Depressed.
- *Vein color* (*abaxial and adaxial surfaces*).—N138D.
- *Leaf length.*—41 cm in length.
- *Leaf width.*—29.50 cm in width.
- *Leaf fragrance.*—None observed to date.
- *Leaf attachment.*—Petiolate.
- *Petiole shape.*—Sulcate.
- *Petiole color.*—144C.
- *Petiole dimensions.*—65 cm in length.

Inflorescence:
- *Flowering months.*—From early June to mid July.
- *Inflorescence type.*—Raceme.
- *Number of flowers per raceme* (*range*).—22-25.
- *Persistent or self-cleaning.*—Self-cleaning.
- *Flower aspect.*—Pendulous.
- *Flower color.*—155B.
- *Flower length.*—5.50 cm in length.
- *Scape length.*—37-38 cm in length.
- *Scape color.*—138A.
- *Scape shape.*—Terete.
- *Scape surface.*—Glabrous.
- *Pedicel color* (*range*).—138A to 138C.
- *Pedicel shape.*—Terete.
- *Pedicel length.*—0.75 cm.
- *Flower shape* (*range*).—Funnel to tubular.
- *Bud shape.*—Clavate.
- *Bud apex.*—Rounded.
- *Bud color.*—155B.
- *Bud length* (*range*).—3 cm to 5 cm in length.
- *Petals.*—Apetalous.
- *Tepals.*—6 in number.
- *Tetals fused or unfused.*—Basally fused.
- *Tepal shape.*—Narrow obovate.
- *Tepal margin.*—Entire.
- *Tepal apex* (*range*).—Acute to rounded.
- *Tepal surface* (*adaxial surface*).—Glabrous.
- *Tepal surface* (*abaxial surface*).—Glabrous.
- *Tepal color.*—155B.
- *Tepal dimensions.*—3.50 cm in length and 1 cm in width.
- *Bract.*—1 per flower bud.
- *Bract shape.*—Navicular.
- *Bract length* (*average*).—2 cm in length.
- *Bract color.*—151B.
- *Bract margin.*—Entire.
- *Bract apex.*—Acute.
- *Flower lastingness.*—Ephemeral.
- *Flower fragrance.*—None observed to date.

Reproductive organs:
- *Stamens.*—6 in number.
- *Stamen color.*—154D.
- *Stamen length.*—3 cm in length.
- *Anther.*—6 in number.
- *Anther color* (*range*).—166A to 166B.
- *Pistil.*—One in number.
- *Pistil shape.*—Filament.
- *Pistil color.*—154D.
- *Stigma color.*—154D.
- *Stigma shape.*—Blunt.
- *Ovary color.*—N144D.
- *Ovary position.*—Superior.

Fruit and seed production:

*Quantity of fruit (seed pods) per lateral branch.*—Approximately 30.

*Fruit shape.*—Cylindrical, three-chambered.

*Fruit color.*—138B.

*Fruit dimensions.*—3.2 cm in length and 7 mm in diameter.

*Quantity of seed.*—Approximately 15 seeds per seed pod.

*Seed shape.*—Flattened oval.

*Seed color.*—202A.

*Seed dimensions.*—1 cm in length and 3.5 mm in diameter.

*Seed surface.*—Dull and slightly ribbed.

It is claimed:

1. A new and distinct variety of *Hosta* plant named 'ECLIPSE' as described and illustrated.

* * * * *